United States Patent [19]

Muszak et al.

[11] Patent Number: 5,283,195
[45] Date of Patent: Feb. 1, 1994

[54] INCUBATOR WITH POSITIONING DEVICE FOR SLIDE ELEMENTS

[75] Inventors: Martin F. Muszak; Gary S. Hartman; Roger G. Leighton, all of Rochester, N.Y.

[73] Assignee: Eastman Kodak Company, Rochester, N.Y.

[21] Appl. No.: 1,876

[22] Filed: Jan. 8, 1993

Related U.S. Application Data

[62] Division of Ser. No. 810,262, Dec. 19, 1991, Pat. No. 5,196,168.

[51] Int. Cl.[5] ............................................. G01N 35/04
[52] U.S. Cl. ............................................ 436/48; 422/63; 422/64; 422/67; 436/46; 436/43
[58] Field of Search ............... 436/46, 43, 48; 422/61, 422/62, 63, 64, 65–67; 435/809

[56] References Cited

U.S. PATENT DOCUMENTS

| | | | |
|---|---|---|---|
| 4,296,069 | 10/1981 | Smith et al. | 422/64 |
| 4,568,519 | 2/1986 | Hamilton et al. | 422/64 |
| 4,826,659 | 5/1989 | Akisada | 422/63 |
| 5,034,191 | 7/1991 | Porte | 422/64 |
| 5,049,359 | 9/1991 | Azuma et al. | 422/64 |
| 5,073,342 | 12/1991 | Porte et al. | 422/64 |
| 5,089,418 | 2/1992 | Shaw et al. | 436/46 |
| 5,102,624 | 4/1992 | Muraishi | 422/64 |

Primary Examiner—James C. Housel
Assistant Examiner—Long V. Le
Attorney, Agent, or Firm—Dana M. Schmidt

[57] ABSTRACT

An incubator useful in an analyzer, and a method for locating a slide element properly in the incubator. The incubator and the method are provided with a referencing mechanism and step, respectively, effective to push back on the datum surface or edge of a slide element that has been inserted too far into a station of the incubator, to move the portion of the slide element that produces a detectable signal, back a distance which is predetermined for that station to be the one that gives the most effective reading of the slide element.

4 Claims, 5 Drawing Sheets

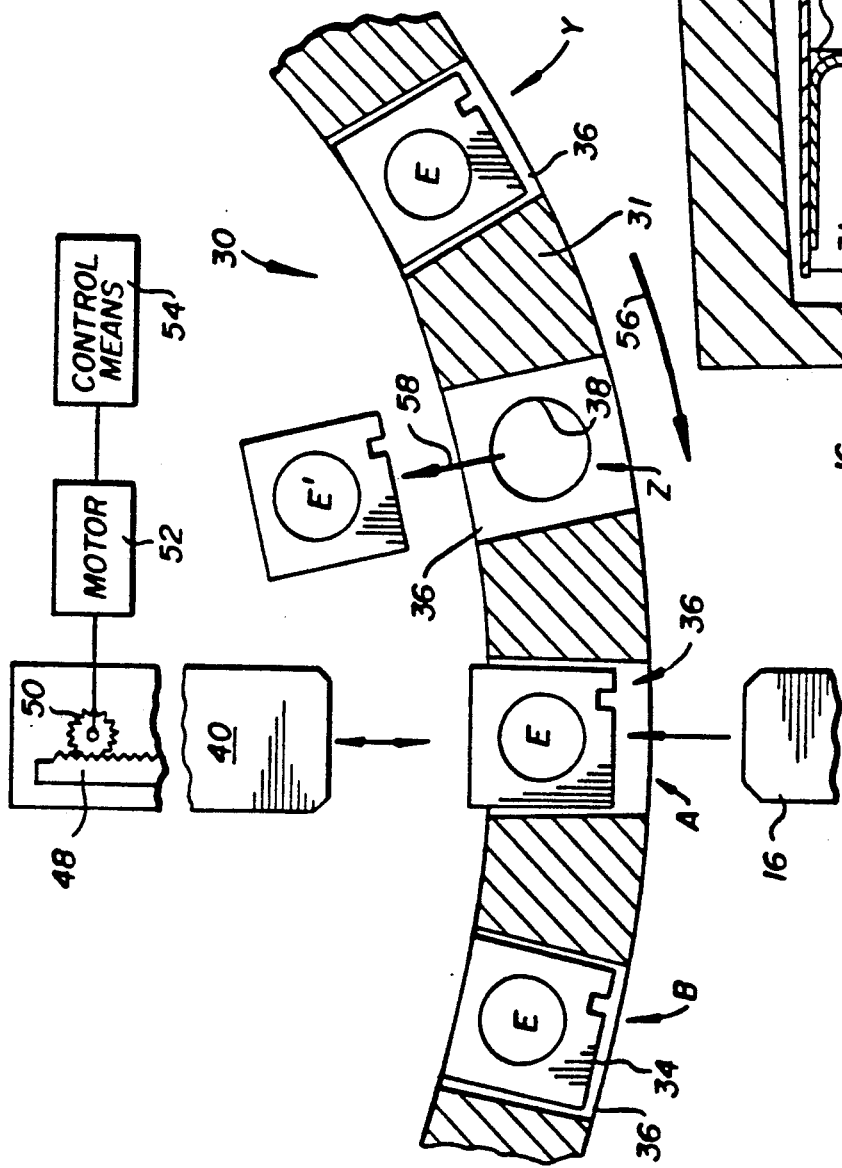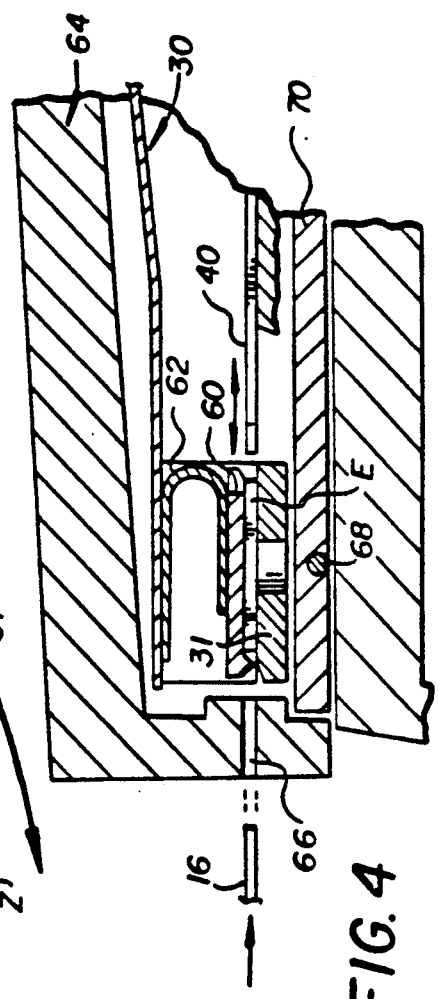

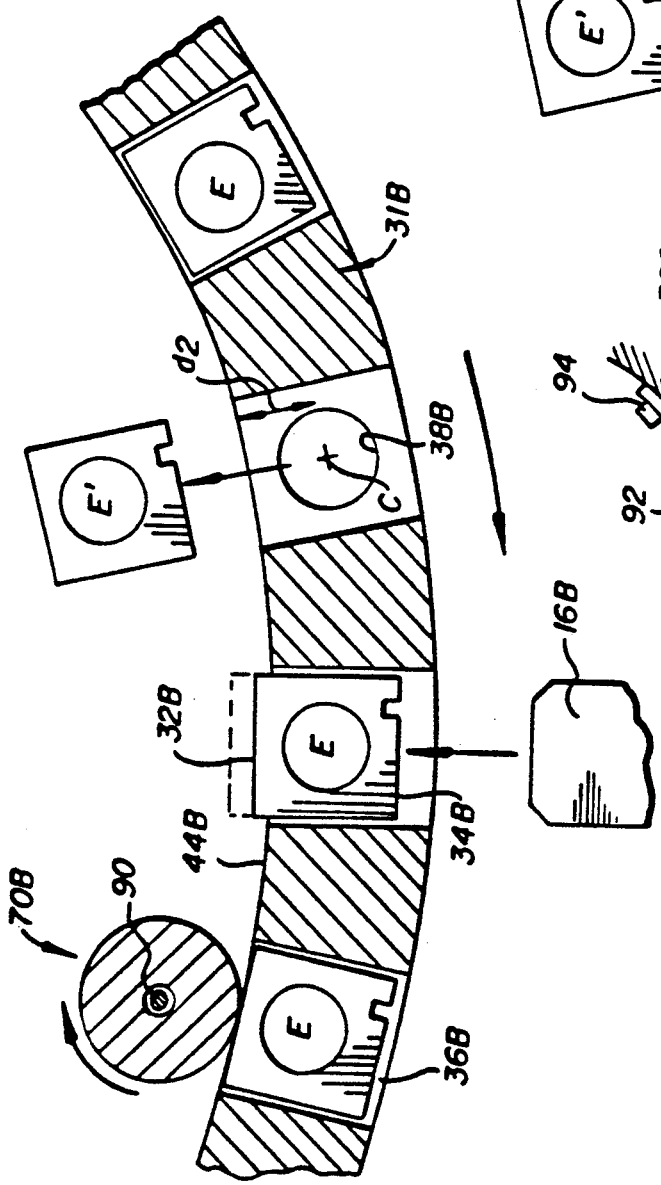
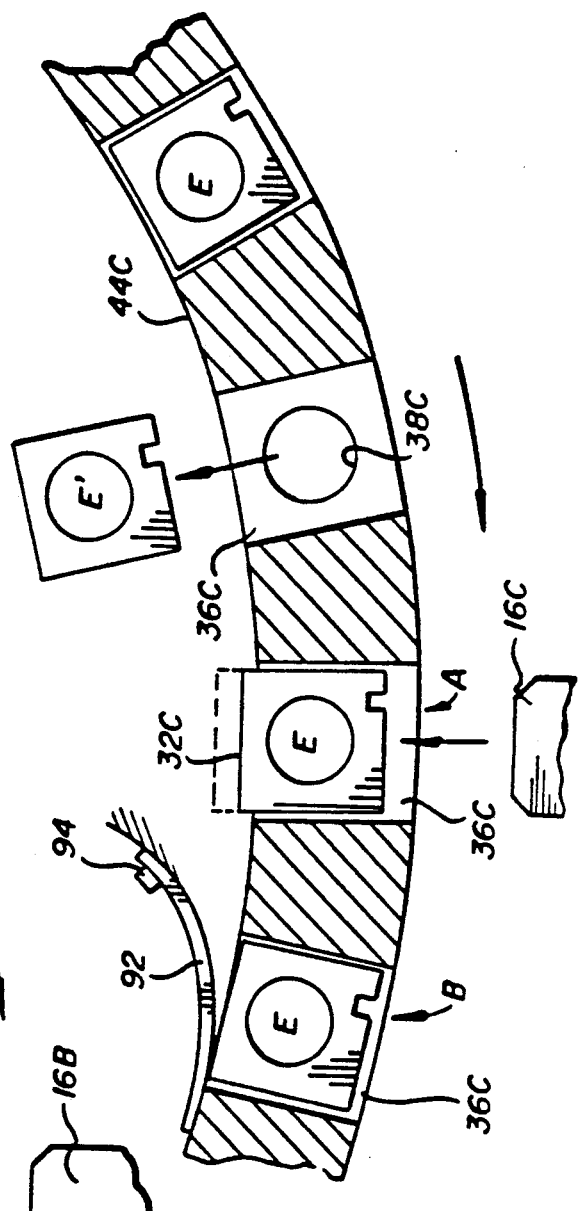

INCUBATOR WITH POSITIONING DEVICE FOR SLIDE ELEMENTS

This is a divisional of application Ser. No. 810,262, filed Dec. 19, 1991, now U.S. Pat. No. 5,196,168.

FIELD OF THE INVENTION

This invention relates to incubators used with clinical analyzers, and especially with the proper positioning of slide elements in such incubators.

BACKGROUND OF THE INVENTION

Incubators for clinical analyzers require test elements, particularly slide-like test elements, to be inserted, incubated, and then removed for analysis. The most common incubator has stations disposed around a rotor such that the same opening into the rotor functions both as an inlet port and an outlet port.

Slide elements conventionally come with one datum or reference surface that is used to ensure the proper location of the element in the analyzer. This datum surface is usually the trailing edge as the element comes off its storage site, which usually is a cartridge. By such means, the pusher blade used to remove the element from its storage can also be used to properly locate the element via its trailing edge at the sample dispensing station. If the element goes immediately from the dispensing station to an incubator, the datum surface is the outer, trailing edge of the element in the rotor. However, in analyzers such as those available from Eastman Kodak Co. under the trademark "Ektachem 700" analyzers, the element is inserted first into an intermediate station, e.g., the slide distributor in the "Ektachem 700" analyzer. When it comes off the intermediate station into the incubator rotor, the datum surface has been reversed and goes in first into the rotor so as to be the inside edge or surface, not the outer edge or surface. The inside datum surface in such analyzers is pushed up against a fixed surface to properly locate it for an incubator reading by a reflectometer. (The surface or edge of the element opposite to the datum surface is not useful, since the length of the slide element can vary.)

Although such fixed incubator surfaces work, they have a disadvantage: It is difficult to control the location of such fixed rotor surfaces, particularly since the rotor may deviate as it rotates about its axis, from being on true center. Such deviations of the rotor during rotation are called "out-of-round" deviations, created by rotor surfaces that are not perfectly concentric with the rotor's center of rotation.

Therefore, there has been a need prior to this invention to control an inside-positioned datum surface of a slide element by means other than a fixed stop.

SUMMARY OF THE INVENTION

We have designed an incubator that avoids the above-noted problems principally by using a referencing mechanism that moves relative to the support in an incubator so as to re-seat a slide element on said support by a fixed distance calibrated to achieve proper centering of the slide elements for reading.

More specifically, in accord with one aspect of the invention, there is provided a rotating incubator in a clinical analyzer, the incubator comprising a support, stations around a circumference of the support constructed to receive a test element for incubation, means for rotating the support, an entrance port permitting access to each of the stations from a location exterior to the rotor, and referencing means interior of the stations in the rotor for locating a datum surface of a slide element inside the rotor. The incubator is improved in that the referencing means comprise a positioning element and means for moving the element relative to the support by pressing against the datum surface to properly locate the surface in the incubator after a slide element is inserted into the station.

In accord with another aspect of the invention, there is provided a method for automatically locating a slide-like test element over a viewing aperture in a support at a station in an incubator, the method comprising the steps of a) loading into the station by a known excessive amount, a reference element having a spot of known density and as its leading edge, a datum surface that is a known distance from the center of the spot, b) scanning the spot through the aperture with a reflectometer, c) pushing the reference element relative to the station until the spot registers a minimum or maximum reflection density at the reflectometer, thus defining a pushed corrective distance, d) storing the corrective distance the reference element is pushed, for the station, e) loading a slide-like test element for a patient analysis into the station by an excessive amount, the datum surface for such test element being the leading surface, and f) pushing it at said datum surface by the amount of the stored corrective distance.

Accordingly, it is an advantageous feature of the invention that an incubator is provided which automatically centers slide elements positioned therein, for reading within the incubator, regardless of "out-of-round" conditions that may exist in the incubator rotor.

It is a further advantageous feature of the invention that it provides such automatic centering, in the most preferred embodiments, with a minimum of impact on the rest of the incubator's functions.

Additional advantageous features will become apparent upon reference to the following Detail Description, when read in light of the attached drawings.

BRIEF DESCRIPTION OF THE DRAWINGS

FIG. 3 is a fragmentary view similar to that of FIG. 2, but showing the annular incubator support that is preferred;

FIG. 4 is a fragmentary side elevational view in section of the incubator of the invention; and FIGS. 5–7 are plan views similar to that of FIG. 3, but of alternate embodiments of the invention.

DESCRIPTION OF THE PREFERRED EMBODIMENTS

The invention is hereinafter described in connection with certain preferred embodiments, wherein a colorimetric slide element is placed onto a rotating incubator support having a generally circular circumference, for reading or detecting a colorimetric change due to an analyte, using an on-line reflectometer detecting station. In addition, it is applicable regardless of the type or chemistry of slide element placed in the incubator, regardless of the configuration of the incubator support, and regardless of the location or type of detection station, as long as the processing of the slide element requires it to be accurately positioned in the incubator. Thus, it is applicable also to ion-selective electrode (ISE) slide elements, for example. In the case of ISE slide elements, the critical part of the slide element is not the center of a dye density, but rather the part where the electrodes are exposed for contact with a potentiometer.

Figure 1:
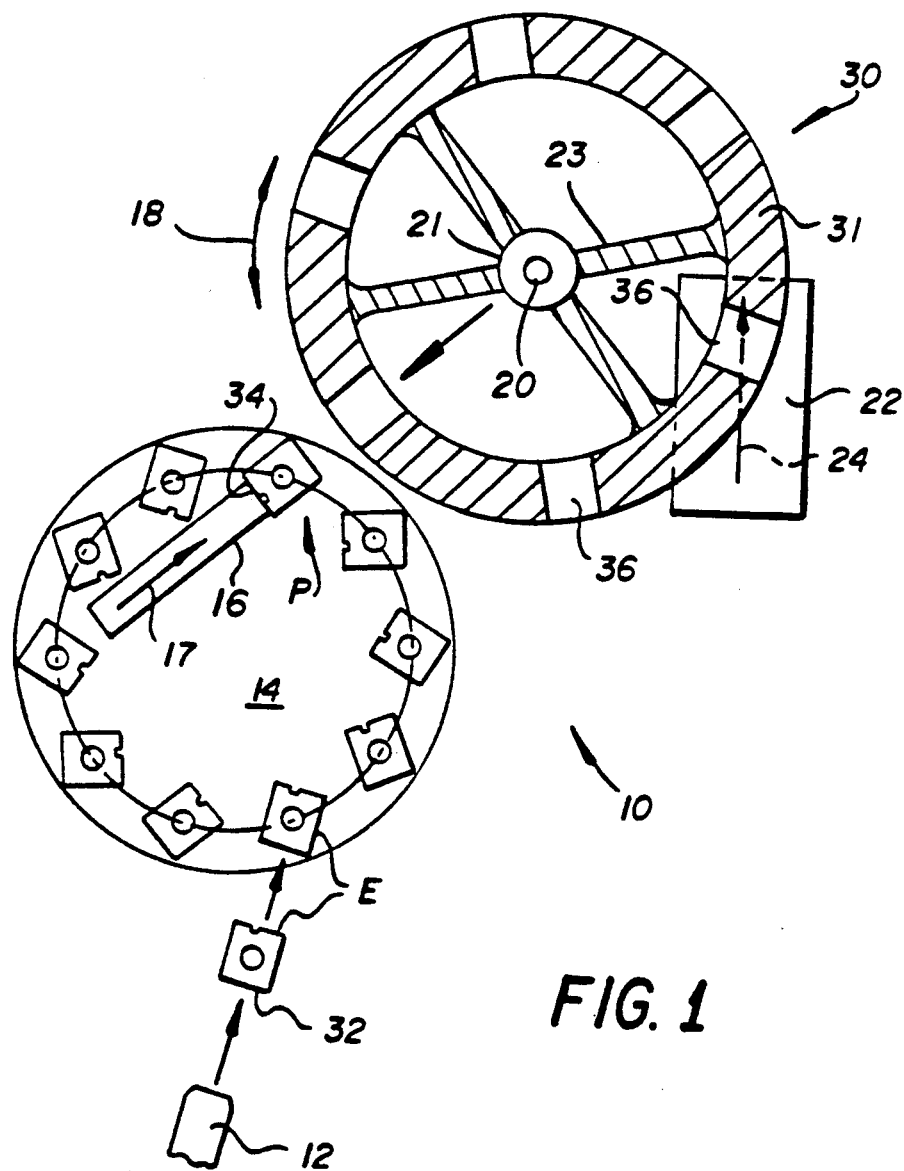
FIG. 1 is a partially schematic plan view of an analyzer illustrating the incubator of the invention.

An analyzer 10, FIG. 1, using an incubator of the invention comprises a pusher blade 12 for loading slide elements "E" onto a preheat station 14, as is conventional, and another pusher blade 16 for transferring such slide elements into incubator 30, arrow 17. Such incubator preferably has an annular support 31 that rotates, arrow 18, as provided by any suitable drive means, e.g., drive shaft 20 that is fixed to a center hub 21 from which shafts 23 extend out to support 31, to carry incubated slide elements to station 22 comprising an on-line reflectometer that conventionally reads color changes in the slide elements, as suggested by arrow 24. Such a construction allows stations 36 to be equidistant from the center of drive shaft 20. Thus, as is evident, slide elements E are preferably colorimetric slides, for example, those available under the registered trademark "Ektachem" from Eastman Kodak Co.

Such slide elements conventionally include a datum surface 32, which is a side edge of the element. Preferably, it is the trailing edge as the element enters station 14. However, as station 14 rotates, elements E end up at position "P" that has reversed the orientation of the element. Thus, when blade 16 engages an element at position "P", datum surface 32 becomes the leading edge or surface of the slide element, rather than the trailing surface.

The geometries involved with datum surface 32 of a given slide element E are more readily understood by reference to FIG. 2. (In this view, the annular support of rotating incubator 30 has been simplified to a linear support for purposes of discussion.) Each datum surface 32 of each element E, as shown for example for element $E_1$, is located a controlled, predetermined distance $d_1$ from the spot center C that has to be properly positioned for proper detection at station 22. (Center C must be properly located over viewing aperture 38.) Spot center C is understood to refer to the expected center of dye development, in colorimetric slide elements, which may or may not coincide with the geometric center of the total slide elements. The spot center in turn is primarily controlled by the dispensing of patient sample onto the slide element, which is conventional.

Importantly, blade 16 pushes against an opposite slide surface 34 that is not a datum surface. That is, manufacturing tolerances are not controlled regarding the distance of surface 34 from center C, so that surface 34 can be drastically varied, in its location, e.g., it can be positioned as shown by the dashed line without altering the position of opposite surface 32 which IS the datum surface.

Surface 34 is shown as having a notch 37 (marked in element $E_1$). This is not an essential feature of either the slide element or the analyzer, as it is used instead as an optional marker during slide manufacturing. However, it is also helpful for visualizing in this discussion as to which slide surface is which.

Incubator support 31 has exterior wall 35, interior wall 44 and a plurality of stations 36 disposed therein and shaped to receive and hold slide elements loaded therein by blade 16. (Springs, not shown, are conventionally included to locate slide elements against one side or the other of the station, in the "x" direction, but not in the "y" direction.)

Because surface 34 is indeterminantly located, as noted above, blade 16 over-drives elements E into the stations 36, as shown in phantom for element $E_2$. Again because of the indeterminant location of surface 34, datum surface 32 is at one of the two dashed line positions shown as 32' or 32", or something in between. Therefore, it is necessary to push elements E back into each station a distance effective to properly center center C of the detecting spot. That is, center C needs to be centered on the viewing aperture 38 at each station 36. (Because the diameter of aperture 38 is much larger than the viewing aperture of the test elements, such apertures 38 are essentially at an invariant distance from either wall 35 or 44.)

Figures 2A, 2B:
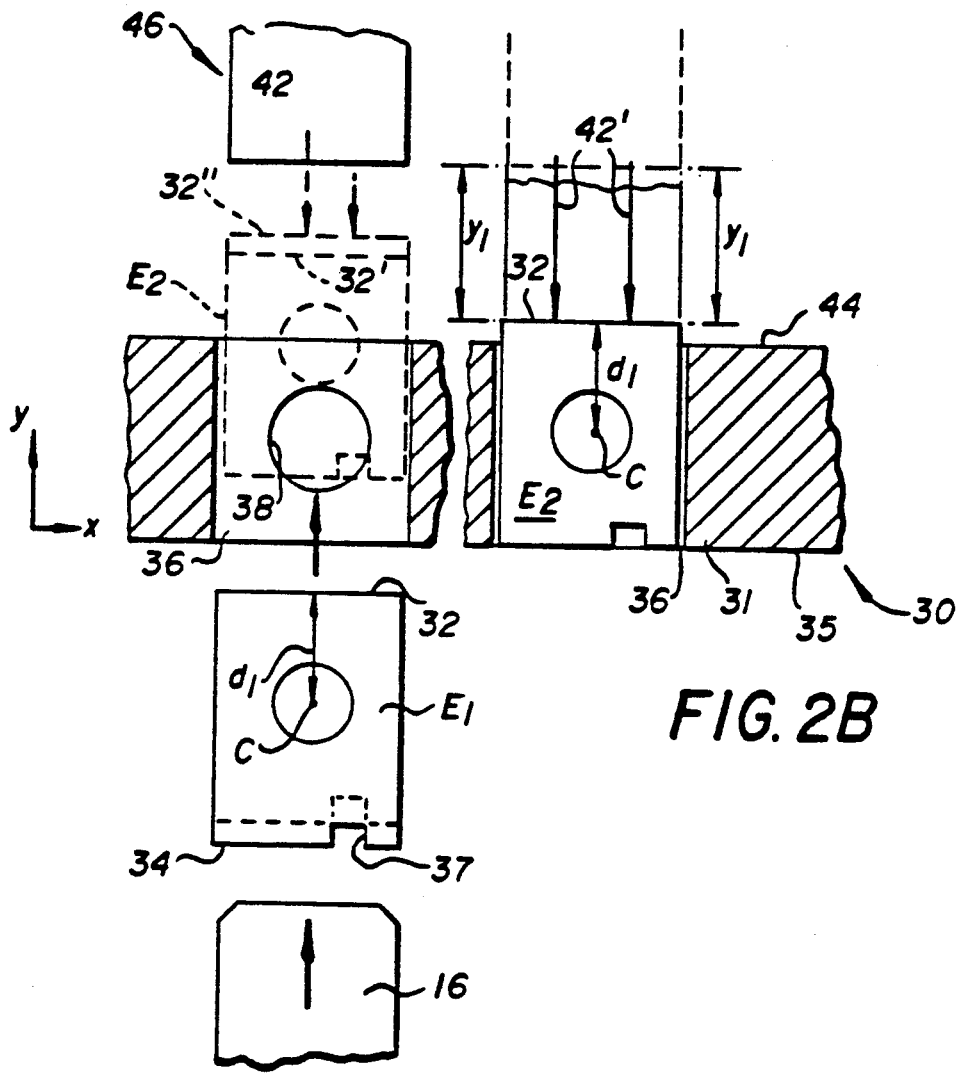
FIGS. 2A and 2B are fragmentary, sequential plan views in section, illustrating the concept of the invention as applied to a non-curved incubator support.

In accordance with one aspect of the invention, a referencing means 40 is provided, FIGS. 2A and 2B, which can have a great variety of shapes and position, as shown hereinafter, and which has been preprogrammed to "know" the distance it has to move back each element E to move center "C" of each slide element so it is centered an aperture 38 for any station 36. For simplicity, means 40 is shown in FIGS. 2A and 2B as a pusher blade, which is in fact one of the preferred embodiments. Blade 40 is positioned at a home position, as shown in solid lines, that preferably remains constant for all stations 36 and which is sufficiently far from the inside of wall 44 of support 31 (inside incubator 30) that no element E ever reaches it upon insertion of the element into its station.

However, control means 54 and drive means 52, FIG. 3, are provided (not shown in FIGS. 2A and 2B) that are used to control the "correcting distance" $y_1$, FIGS. 2A and 2B, that blade 40 has to move for each respective station 36, etc. to reposition an element E with center C centered on aperture 38. That distance is preassigned in the manner defined hereinafter, and thereafter used for all stations. As will be apparent, the same value $y_1$ is useful for all stations 36, etc., once it is predetermined.

Thus, blade 40 (or whatever device is used) pushes, such as by advancing arrows 42, FIG. 2A, against the datum surface 32 of element E, back into the station so that each slide is properly centered, as shown, FIG. 2B. In the case of element $E_2$, distance $y_1$ moved by arrow 42' is sufficient because distance $d_1$ for any element at station 36 sufficient to center center C, has been predetermined.

At least in the case of a pusher blade 40, distance $y_1$ can be even large enough to relocate datum surface 32 inbetween walls 35 and 44 of support 31.

Thus, FIG. 3, a preferred construction is one in which incubator support 31 comprises an annular ring and referencing means 40 comprises a pusher blade driven, e.g., by a rack 48 mounted on top that engages a pinion gear 50 driven by a conventional stepper motor 52 controlled by control means 54. The last is preferably part of the computer(s) of analyzer 10. Blade 40 then acts in opposition to blade 16, when station 36 is at position A as shown. Recentering occurs as described above, elements E at stations B and Y having already been recentered. Rotation of incubator 30 is in the direction of arrow 56, so that station Z is a dump station, arrow 58. Station Y is, for example, the read station where the reflectometer (not shown) is located underneath support 31.

The predetermined value of $y_1$ described above, that is preassigned for any station 36 is ascertained in the following manner:

A reference slide element having a spot of known optical density of any color (i.e., readable at a selected wavelength) is positioned in a given station 36 of the incubator by blade 16, that is, is overdriven to the phantom position shown in FIG. 2A. It can be assumed, e.g., the spot of density is a "dark" spot giving off minimum reflectance when properly scanned. However, the process works as well for a so-called "light" or "white" reference that reflects a maximum amount of light if properly read, provided that the rest of the test element is dark in color to produce a non-reflecting background. This element has the same predetermined and fixed distance $d_1$ from its leading datum edge or surface (32 in FIG. 2A) to the center C of its spot of known density, as the value of $d_1$ for the test elements to be later used. At this point in the incubator of FIG. 3, the reference element occupies station A. Support 31 is then rotated, e.g., in the direction of arrow 56, until the reference element E is carried to station Y, the read station, and the reflected density is detected.

Because the spot of the reference element is NOT properly centered at this time (blade 40 having remained inactive), the detected reflectance at this reading will NOT be a minimum (in the case of a dark reference spot).

Support 31 is again rotated to return the reference element to station A. At this time, blade 40 is activated to at least contact and move the reference element back slightly, e.g., about 1-2 mm, into its station 36. Stepper motor 52 allows a certain number of half steps to be used. Blade 40 is then withdrawn a recorded amount, and support 31 rotated to return the reference element to station Y for a second reading.

This process is iterated until a minimum density is reflected from the reference element, thereby indicating that its spot is indeed centered over the viewing aperture having that particular location for all stations. The "$y_1$" distance used, FIG. 2A, is recorded by control means 54 as a certain number of half steps used by stepper motor 52 to achieve the "$y_1$" distance corrective return of the element into its incubator station. That "$y_1$" corrective distance thereafter is the push-back distance to be used for all stations 36.

Thereafter, test elements E bearing patient sample need only be over-inserted into that station and then pushed back by blade 40 the corrective distance. Because the corrective movement of blade 40 is independent of the initial location of datum surface 32, the correction is accurate regardless of the excessive in-feed that occurs via blade 16 and the indeterminant location of opposite edge or surface 34. Each corrective distance is essentially the same for all stations, due to the proper centering of the essentially annular support 31.

In the embodiment of FIG. 3, and all those hereinafter described, a cover 60, FIG. 4, is biased onto elements E at each station, by a spring 62. The cover and spring can be any convenient shape, for example the shapes as described in commonly owned allowed U.S. Ser. No. 527,501 filed on May 23, 1990, entitled "J-Shaped Spring Used in Incubator" and in corresponding EPA publication 458406. The details of that application and publication are expressly incorporated herein. Cover 60 is used to prevent undue evaporation of sample from element E, as is conventional. The shape of cover 60, and that of spring 62, are not important, other than the cover must allow slide element E to be pushed farther out towards blade 40 than is shown in FIG. 4. Rotor 30 is sealed within a housing 64, except for an inlet passage 66 through which elements E and blade 16 pass. Temperature control occurs, e.g., via a heating cable 68 located in a temperature platen 70 disposed under support 31.

Figure 5:
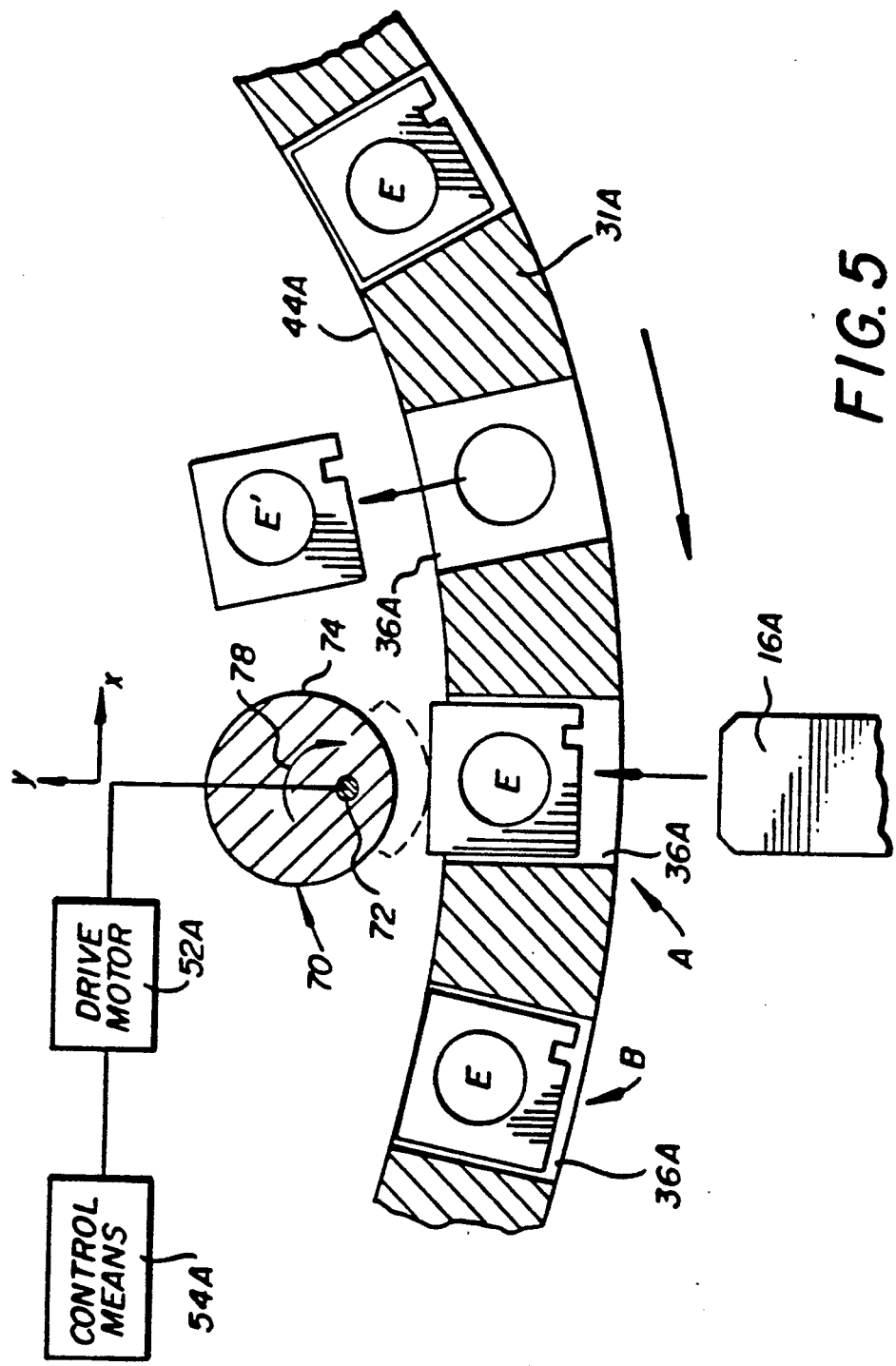

Referencing means 40 need not be a pusher blade, but can have a variety of shapes. A roller is also useful, FIG. 5. Parts similar to those previously described bear the same reference numeral, to which the distinguishing suffix "A" is appended. Thus, incubator support 31A is constructed as described above, with interior wall 44A and stations 36A to receive test elements as they are fed in at position "A" by blade 16A an excessive amount.

However, in this embodiment the referencing means to push back each element E a corrective distance comprises a roller 70, preferably one that is eccentrically mounted on a drive shaft 72 that in turn is rotated by drive motor 52A as controlled by control means 54A. Also preferably, roller 70 has a generally cylindrical side wall 74. As before, motor 52A is preferably a stepper motor. Because of the concentric mounting of roller 70, a certain amount of angular rotation (arrow 78) of shaft 72 is effective to contact an element E (as shown in phantom) and move it back the needed corrective distance "y", as described above. Most preferably, side wall 74 contacts a slide element E at the middle of the element's side edge, to prevent cocking of the element.

Still further, it is not necessary that roller 70 be located generally opposite blade 16A, that is, at position A. It can optionally (not shown) be located opposite any position, e.g., position B to achieve the same results, assuming other parts of the incubator permit each positioning.

Yet another alternate embodiment is to have roller 70 be centrally journalled on shaft 72, where shaft 72 is now an idler shaft (not shown). In such an embodiment, drive motor 52 would be used to alter the location in the "y" direction, FIG. 5, of the axis of idler shaft 72, thereby allowing roller 70 to freely rotate at an adjustable but constant distance from wall surface 44A. This then would cause elements E that have been overdriven into stations 36A, to be pushed back by the roller.

Carrying this concept one step further, and relying on the incubator support 31 having its inside wall surface 44 being substantially cylindrical and properly centered, that is, not "out-of-round", the referencing means can operate a fixed distance, and specifically the distance needed simply to align datum surface 32 with the inner wall surface 44, FIGS. 6 or 7. In this alternate embodiment, parts similar to those previously described bear the same reference numeral to which the distinguishing suffix "B" or "C", respectively, is appended.

Thus, FIG. 6, the referencing element can comprise a roller 70B, used with support 31B having an interior wall 44B and stations 36B as before to receive test elements E from blade 16B, as before. Also as before, datum surface 32B initially projects beyond wall 44B an indeterminant distance, optionally as much as the position shown in phantom, due to the uncertain location of the opposite, non-datum surface 34B. However, because the viewing aperture 38B is much larger than the corresponding viewing aperture of the test elements, and distance $d_2$ is adjusted to correspond to distance $d_1$, carefully controlled as noted above, all that is needed is to have datum surface 32B pushed back to be tangent to wall 44B. Hence, roller 70B is concentrically journalled for free rotation on idler shaft 90. Its function is simply to roll (in place) along wall 44B as the latter travels past it, and to "kiss" projecting elements E by a wiping action, back into their stations enough to achieve this alignment.

In FIG. 7, the referencing means comprise a wiping blade 92 fixed by appropriate means 94 to wipe opposite station B along interior wall 44C, thereby to realign datum surface 32C with that wall. Otherwise, stations 36C, aperture 38C, support 31C and blade 16C function as described before. However, this option is less preferred than the alternative of FIG. 6, due to increased friction.

Both the embodiments of FIGS. 6 and 7 are less preferred than those previously described, in part due to the fact that they can cause slide element E to be "cocked" in its station, and in part because surface 44B can be out of round.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A method for automatically locating a slide test element over a viewing aperture in a support at a station in an incubator, the method comprising steps of
   a) loading into said station a reference element having a spot of known density and a datum surface as a leading edge of the reference element, said datum surface being a known distance from a center of said spot, said loading step comprising inserting said reference element so as said center of said spot is beyond a center of said viewing aperture of said station,
   b) scanning said spot through said aperture with a reflectometer,
   c) pushing said reference element relative to said station until said spot registers a minimum or maximum reflection density at said reflectometer, thus defining a pushed corrective distance,
   d) storing the corrective distance said reference element is pushed, for said station,
   e) loading a slide test element for a patient analysis into said station wherein said a center of said slide test element is inserted beyond said center of said viewing aperture, a datum surface for said test element being a leading edge, and
   f) pushing said slide test element at said datum surface by an amount of said stored corrective distance.

2. A method as defined in claim 1, wherein said steps b) and c) comprise i) moving said support and reference element to a read position in which said support is disposed over a reflectometer, ii) reading the density, iii) moving said support and reference element to a different position at which the reference element can be incrementally pushed part of said corrective distance, iv) returning said support and reference element to said read position, and reiterating steps ii), iii) and iv) until a minimum or maximum density is recorded by said reflectometer and said reference element has been pushed said corrective distance.

3. A method as defined in claims 1 or 2, wherein said steps c) and f) comprise pushing on an element at said station with a pusher blade.

4. A method as defined in claims 1 or 2, wherein said steps c) and f) comprise pushing on an element at said station with a member rotatably mounted on a shaft.

* * * * *